(12) United States Patent
Wachtel et al.

(10) Patent No.: US 9,295,792 B2
(45) Date of Patent: Mar. 29, 2016

(54) INHALER

(71) Applicants: Vectura Delivery Devices Limited, Chippenham (GB); BOEHRINGER INGELHEIM INTERNATIONAL GMBH, Ingelheim am Rhein (DE)

(72) Inventors: Herbert Wachtel, Ingelheim am Rhein (DE); Quentin John Harmer, Chippenham (GB); Matthew Neil Sarkar, Chippenham (GB); Ivan Milivojevic, Chippenham (GB)

(73) Assignees: VECTURA DELIVERY DEVICES LIMITED, Chippenham (GB); BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 0 days.

(21) Appl. No.: 14/483,788

(22) Filed: Sep. 11, 2014

(65) Prior Publication Data

US 2014/0373839 A1 Dec. 25, 2014

Related U.S. Application Data

(63) Continuation of application No. 12/864,527, filed as application No. PCT/EP2008/011126 on Dec. 29, 2008, now abandoned.

(30) Foreign Application Priority Data

Jan. 24, 2008 (EP) ..................................... 08001298

(51) Int. Cl.
*A61M 15/00* (2006.01)
*A61M 11/00* (2006.01)

(52) U.S. Cl.
CPC .......... *A61M 15/0005* (2014.02); *A61M 11/002* (2014.02); *A61M 15/0008* (2014.02);

(Continued)

(58) Field of Classification Search
CPC ............ A61M 15/00; A61M 15/0001; A61M 15/0005–15/001; A61M 15/002–15/0021; A61M 15/0028–15/003; A61M 15/0033–15/0041; A61M 15/0045–15/0051
See application file for complete search history.

(56) References Cited

U.S. PATENT DOCUMENTS 2,470,297 A 5/1949 Fields
5,590,645 A * 1/1997 Davies et al. ............ 128/203.15
(Continued)

FOREIGN PATENT DOCUMENTS

CA 2509845 7/2004
CA 2558564 12/2005
(Continued)

OTHER PUBLICATIONS

Decision of Rejection, dated Nov. 5, 2013, issued by the Japanese Patent Office in connection with corresponding Japanese Application 2010-543388.

(Continued)

*Primary Examiner* — Rachel Young
(74) *Attorney, Agent, or Firm* — Davidson, Davidson & Kappel LLC

(57) ABSTRACT

A passive inhaler for delivery of a powder-form inhalation formulation from a blister strip with a plurality of blister pockets is proposed. The inhaler includes an impaction element onto which the air stream can impact together with entrained inhalation formulation for better deagglomeration. Alternatively, the inhaler includes an oscillating and/or vibrating device for better de-agglomeration of the inhalation formulation. Alternatively or additionally, the inhaler includes one or two mixing means for generating swirls, preferably with opposite rotation directions.

11 Claims, 6 Drawing Sheets

Figure 1:
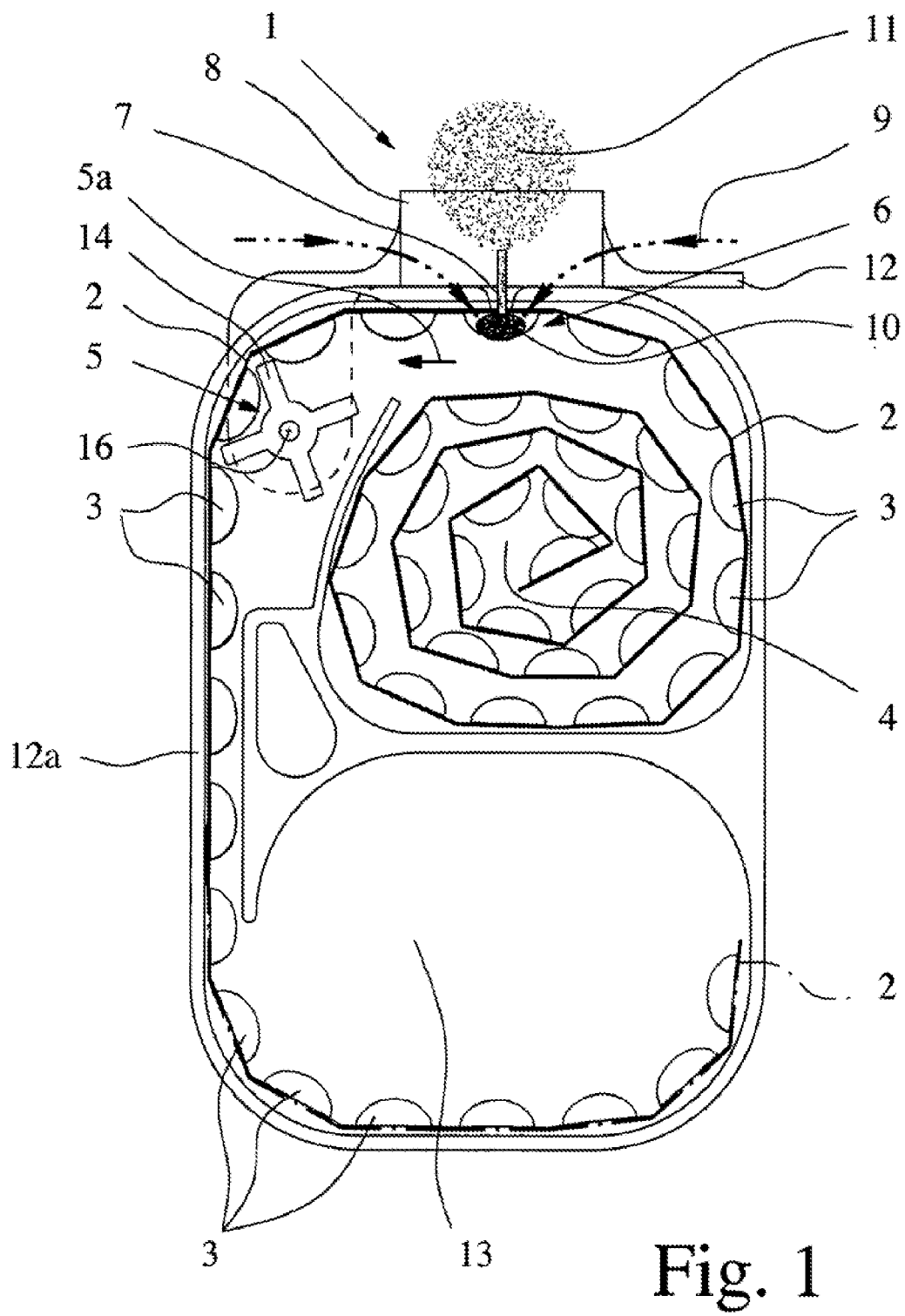
Figure 2:
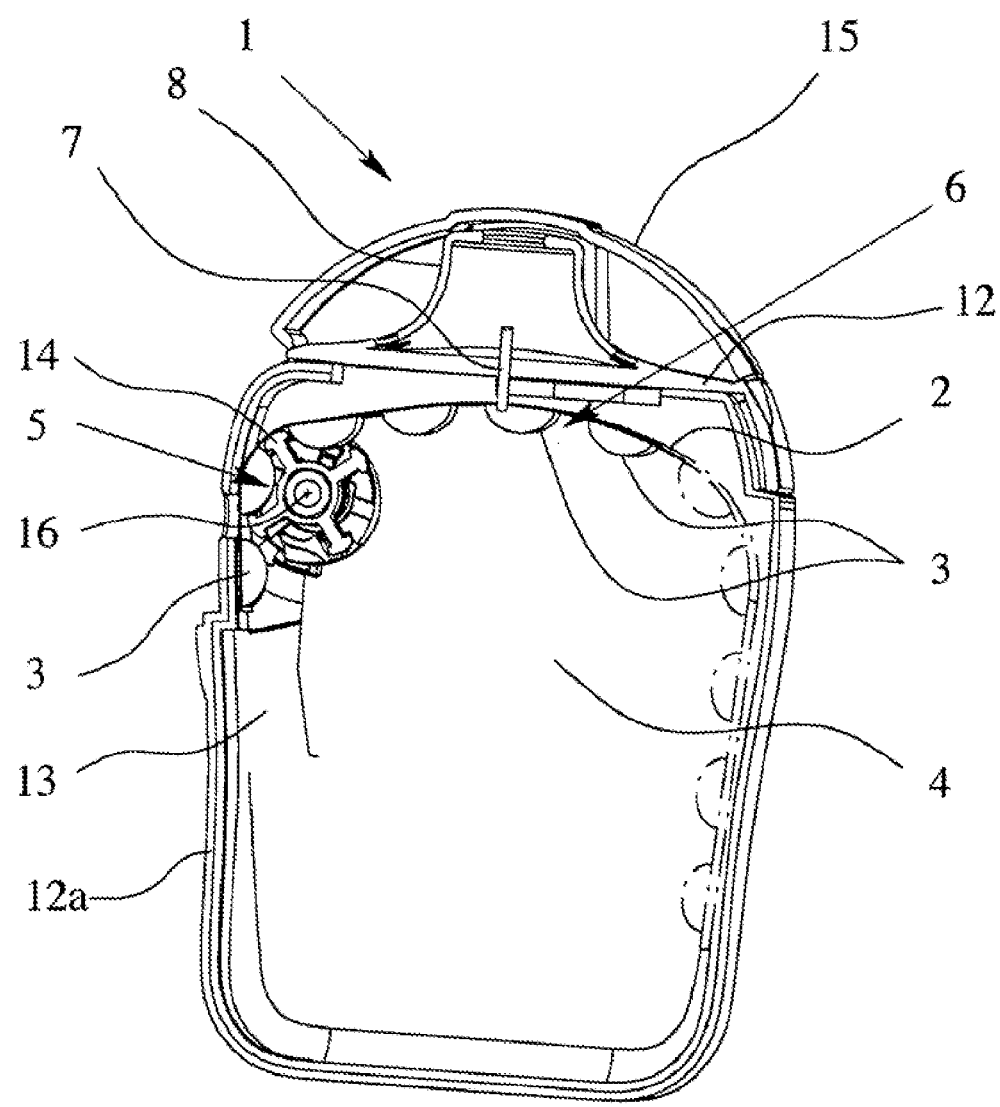

(52) U.S. Cl.
CPC ......... *A61M15/009* (2013.01); *A61M 15/0026* (2014.02); *A61M 15/0045* (2013.01); *A61M 15/0051* (2014.02); *A61M 15/0055* (2014.02); *A61M 15/0058* (2014.02); *A61M 15/0085* (2013.01); *A61M 2202/064* (2013.01); *A61M 2206/16* (2013.01)

(56) References Cited

U.S. PATENT DOCUMENTS

| | | | |
|---|---|---|---|
| 5,622,166 | A | 4/1997 | Eisele et al. |
| 5,921,237 | A | 7/1999 | Eisele et al. |
| 6,065,472 | A | 5/2000 | Anderson et al. |
| 6,347,629 | B1 | 2/2002 | Braithwaite |
| 6,470,884 | B2 * | 10/2002 | Horlin ............... 128/203.15 |
| 2001/0027790 | A1 * | 10/2001 | Gieschen et al. ........ 128/203.15 |
| 2006/0254583 | A1 | 11/2006 | Deboeck et al. |
| 2007/0137645 | A1 | 6/2007 | Eason et al. |
| 2007/0240714 | A1 | 10/2007 | Dunne et al. |
| 2008/0163868 | A1 | 7/2008 | Pocock et al. |
| 2009/0013994 | A1 | 1/2009 | Jones et al. |
| 2011/0132358 | A1 | 6/2011 | Eason et al. |

FOREIGN PATENT DOCUMENTS

| | | |
|---|---|---|
| CA | 2483800 | 7/2012 |
| FR | 2881118 | 7/2006 |
| GB | 2407042 A | 4/2005 |
| JP | 2000503565 | 3/2000 |
| JP | 2001-506885 | 5/2001 |
| JP | 2001-187143 | 7/2001 |
| JP | 2002-537952 | 11/2002 |
| JP | 2005-520603 | 7/2005 |
| JP | 2005-532091 | 10/2005 |
| JP | 2006-512958 | 4/2006 |
| JP | 2007533363 | 11/2007 |
| WO | WO 95/03846 | 2/1995 |
| WO | WO 9725086 | 7/1997 |
| WO | WO 9726934 | 7/1997 |
| WO | WO98/26827 | 6/1998 |
| WO | WO 02/056948 | 7/2002 |
| WO | WO 03/000325 A1 | 1/2003 |
| WO | WO 2004/110538 A1 | 12/2004 |
| WO | WO 2005037353 A1 | 4/2005 |
| WO | WO2007/096111 | 8/2007 |
| WO | WO 2007/118490 | 10/2007 |

OTHER PUBLICATIONS

Office Action dated Jan. 29, 2013, from the Japanese Patent Office concerning the corresponding Japanese Application No. 2010-543388.
The International Search Report issued in corresponding International Patent Application No. PCT/EP2008/011126.
European Search Report in corresponding European Application No. 15176648.2, dated Nov. 26, 2015.

* cited by examiner

INHALER

The present invention relates to an inhaler according to the preamble of one of the independent claims.

The present invention relates to an inhaler for delivery of a powder-form inhalation formulation from a blister strip with a plurality of blister pockets (also called blisters) containing the inhalation formulation in doses.

GB 2 407 042 A discloses an inhaler with a rolled-up blister strip. The inhaler comprises a manually operated, pivotable actuator, which operates a conveyor for stepwise moving the blister strip. The actuator supports a piercer and an associated mouthpiece. By pivoting the actuator, the blister strip and be moved forward and blister pockets of the blister strip can be pierced one after) the other. When a patient breathes in an air stream passes through the previously pierced blister pocket, with the result that the inhalation formulation in the blister pocket mixes with the air and is discharged to the patient.

The present invention relates to passive inhalers, i.e. inhalers where the patient or user breathes in to generate an air stream, which entrains the inhalation formulation and forms the desired aerosol. Problematic is the deagglomeration of the inhalation formulation and to ensure that the aerosol mainly contains only fire particles, preferably in the range of 2 to 10 μm, in particular 2 to 7 μm, of the inhalation formulation.

Object of the present invention is to provide an inhaler with optimized discharge characteristics.

The above object is achieved by an inhaler according to one of the independent claims. Advantageous embodiments are subject of the subclaims.

According to a first aspect of the present invention, the inhaler comprises an impaction element for impaction and/or deflection of the air stream with entrained inhalation formulation, This allows optimization of the discharge characteristics. in particular, larger particles of the inhalation formulation can impact onto the impaction element and, thus, in particular split up into finer particles.

According to a second aspect of the present invention, which can be realized independently, the inhaler comprises a mixing means for generating a swirl or cyclone of air within the inhaler. This supports better mixing and in particular deagglomeration of larger particles of the inhalation formulation entrained by the air.

Most preferably, the impaction element and the mixing means are combined in order to achieve optimized discharge characteristics. Then, the mixing means is preferably located upstream of the impaction element.

According to a further aspect of the present invention, which can be realized in combination with or independent on the above aspects, two mixing means for generating swirls or cyclones with opposite direction of rotation are provided. In particular, the two mixing means are arranged one after the other or axially one above the other. Thus, optimized de-agglomeration of the inhalation formulation can be achieved.

According to another aspect of the present invention, the inhaler comprises alternatively or additionally an oscillating and/or vibrating device for supporting de-agglomeration of the inhalation formulation and/or for vibrating the blister, a feeding path, a piercing member or any other component of the inhaler. This enables or ensures better de-agglomeration of the inhalation formulation and, thus, optimized discharge characteristics.

Preferably, the oscillating and/or vibrating device comprises an oscillating element, such as a ball, located within or upstream the feeding path and being operated by the air stream flowing through the inhaler, in particular its feeding path, when the inhaler is operated or used.

In particular, the oscillating and/or vibrating device and/or its oscillating element forms an impaction and/or deflector means, which supports de-agglomeration of in particular large particles of the inhalation formulation entrained by the gas stream flowing through the feeding path and, in particular, impacting onto the oscillating element.

Alternatively or additionally, the oscillating and/or vibrating device sets in vibration preferably at least part of the inhaler and/or blister strip, in particular the feeding path, a piercing member and/or the respective blister pocket itself. This allows or ensures optimized loosening and/or de-agglomeration of the inhalation formulation from the reservoir, in particular blister pocket.

Preferably, the inhaler comprises in addition to or in combination with the oscillating and/or vibrating device also a mixing means for generating a swirl or cyclone, preferably in the feeding path. In particular, this mixing means is located upstream the oscillating and/or vibrating device. This combination allows achievement of very good discharge characteristics, in particular much better de-agglomeration of the inhalation formulation than the prior art.

Further aspects, features, properties and advantages of the present invention are described in the claims and the subsequent description of preferred embodiments, with reference to the drawing. There are shown in:

FIG. 1 a schematic sectional view of an inhaler without mouthpiece cover;

FIG. 2 a schematic sectional representation of the inhaler with closed mouthpiece cover;

FIG. 3 an enlarged sectional view of the inhaler in the region of a mouthpiece and a piercing member;

FIG. 4 a sectional view of an insert within the mouthpiece;

FIG. 5 an enlarged sectional view of another inhaler in the region of a mouthpiece and a piercing member; and FIG. 6 an enlarged sectional view of a further inhaler in the region of a mouthpiece and a piercing member.

In the Figures, the same reference numbers are used for identical or similar parts, even if a repeated description is omitted. In particular identical or corresponding advantages and properties then also result or may be achieved.

FIG. 1 shows in a schematic sectional representation an inhaler 1. Preferably, the inhaler 1 is portable, works only mechanically and/or is hand-held.

The inhaler 1 serves to deliver a powdered inhalation formulation from a band-shaped blister strip 2. The blister strip 2 is finite, not forming an endless or closed loop. It has a large number of blister pockets 3 respectively containing directly a dose of the loose inhalation formulation. Thus, the formulation is pre-metered.

The inhaler 1 has a reservoir 4 for the still unused blister strip 2 with closed (sealed) blister pockets 3. The blister strip 3 is rolled up or wound up in the reservoir 4. In the representation example the reservoir 4 is formed such that the blister strip 2 can be moved outwards or pulled out of the reservoir 4 as easily as possible.

In the representation example the blister strip 2 is directly received in the reservoir 4. However, instead of this a cassette, a container, a drum or suchlike can also be fitted or inserted with the blister strip 2 into the inhaler 1 or the reservoir 4.

The inhaler 1 has a conveyor 5 for stepwise onward movement of the blister strip 2 in direction of arrow **5*a* by one blister pocket 3, in order to feed the blister pockets 3 successively to an opening and/or removal position 6 where the respective blister pocket 3** is opened and can be emptied.

The blister pockets 3 can be opened respectively preferably by means of a piercing member 7 which punctures or cuts open a lid of the respectively aligned blister pocket 3 in position 6. The piercing member 7 is hollow and/or in fluid connection with an adjacent mouthpiece 8 of the inhaler 1.

During or for inhalation a patient or user, not represented, places the mouthpiece 8 in his mouth and breathes in. The respectively opened blister pocket 3, into which the piercing member 7 extends, is thereby emptied by sucking in. An air stream 9 of ambient air is sucked in and passed through the opened blister pocket 3 such that loose powder 10 (forming the inhalation formulation and being schematically shown in FIG. 1 only in the actually opened blister pocket 3 below mouthpiece 8) is dispensed with the sucked-in ambient air as an aerosol cloud 11 via the mouthpiece 8. This situation is schematically represented in FIG. 1.

The inhaler 1 has a preferably manually actuatable, lever-like actuator 12 being pivotally mounted to a housing 12a of the inhaler 1. The piercing member 7 and the mouthpiece 8 are attached to and supported by the actuator 12.

The actuator 12 is operable (pivotable) to cause the piercing member 7 to puncture the lid of the respectively aligned blister pocket 3 in position 6 below the mouthpiece 8.

When the actuator 12 swivels from the position shown in FIG. 1 (here anti-clockwise) to the partially opened position shown in FIG. 3, the piercing member 7 is withdrawn from the last-pierced blister pocket 3.

Then, the blister strip 2 is moved forward by one blister pocket 3, so that the next blister pocket 3 is moved in position 6. This will be explained in more detail later.

When the actuator 12 swivels back into the position shown in FIG. 1, i.e. is manually moved back, the next aligned blister pocket 3 of the blister strip 2 is punctured by the piercing member 7 and thereby opened. Then, the next inhalation can take place, i.e. the inhaler 1 is activated.

The inhaler 1 has a receiving space or apparatus 13 to receive or store the used part of the blister strip 2. The receiving space or apparatus 13 is formed such that the used part can be wound up. FIG. 1 shows a situation with essentially filled reservoir 4 and still essentially empty receiving space 13.

The conveyor 5 comprises a conveying wheel 14, which can engage between the blister pockets 3 and thus convey the blister strip 2 in form-locking or form-fit manner. This allows very secure or precise moving or indexing of the blister strip 2 as desired and/or necessary.

The conveyor 5 or its conveying wheel 14 is arranged between the reservoir 4 and the receiving apparatus 13, in particular between the removal position 6 and the receiving apparatus 13, thus after the emptying of the blister pockets 3.

The pivot axis of the actuator or lever 12 is coaxial with the rotation axis of the conveying wheel 14. In particular, the actuator or lever 12 may be supported by an axle of the conveying wheel 14.

The inhaler 1 comprises a mouthpiece cover 15. The mouthpiece over 15 is not shown in FIG. 1, which explains only the basic principle of the inhaler 1, but in FIG. 2, which shows a more realistic, but still schematic sectional view of the inhaler 1. FIG. 2 shows the inhaler 1 with closed mouthpiece cover 15, wherein the blister strip 2 has been partly omitted for illustration purposes. FIG. 3 shows the inhaler 1 with completely opened mouthpiece cover 15.

The mouthpiece cover 15 is pivotable around a cover axis 16, which is indicated in FIGS. 2 and 3 and extends perpendicular to the drawing plane in the present representation.

The pivot axis of the actuator 12 extends coaxial to or with the cover axis 16. The rotation axis of the conveying wheel 14 extends coaxial to the cover axis 16 and to pivot axis of the actuator 12.

The conveyor 5 or its conveying wheel 14 is driven by the mouthpiece cover 15, namely by the pivotal movement of the mouthpiece cover 15. In particular, the blister strip 2 is moved forward, when the mouthpiece cover 15 is opened. Preferably, only part of the opening movement of the mouthpiece cover 15 actuates or operates the conveyor 5 or its conveying wheel 14 to move the blister strip 2 forward, FIG. 3 shows in an enlarged sectional view the piercing member 7 with the mouthpiece 8 and an opened blister pocket 3 in the removal position 6. it can be seen that the piercing member 7 or inhaler 1 preferably comprises an insert 17, which is connected to the mouthpiece 8 and, in particular, extends into an outlet space or tube 18 of the mouthpiece 8.

The insert 17 is located adjacent to the piercing member 7. In particular, the piercing member 7 forms or holds the insert 17 or vice versa.

Preferably, the insert 17 is held form-fit within the mouthpiece 8 or its outlet tube 18. However, other construction solutions are also possible.

The inhaler 1 or mouthpiece 8 comprises preferably at least one, here multiple air openings 19 through which the air stream 9 of ambient air can flow in.

The piercing member 7 and the mouthpiece 8 and/or the insert 17 form a feeding path 20 for the air which has been flown through the opened blister pocket 3 and, in addition, a bypass path 21 for air bypassing the blister pocket 3. Both paths 20 and 21 end preferably within the mouthpiece 8 or its outlet tube 18 and/or at a mixing zone 22 where the respective streams through the paths 20 and 21 mix.

In particular, the air stream 9 entering through the air openings 19 is split up into a feeding air stream 23 flowing through the opened blister pocket 3 and then through the feeding path 20, and into a bypass air stream 24 flowing through the bypass path 21.

FIG. 3 shows schematically the aerosol generation when the air flows. The feeding air stream 23 flowing through the opened blister pocket 3 entrains the inhalation formulation (powder 10) and flows into the mouthpiece 8 or its outlet tube 18, in particular to the mixing zone 22 where it mixes with the bypass air stream 24. Thus, the aerosol cloud 19 is generated as schematically shown in FIG. 3.

In the present embodiment, the piercing member 7 preferably comprises at least one, here two piercer elements 25 and 26 as shown in FIG. 3.

The first piercing element 25 serves to form a first blister opening (inlet opening) in a lid 27 of the blister pocket 3 as shown in FIG. 3. The second piercing element 26 forms a separate, second blister opening (outlet opening) in the lid 27 as schematically shown in FIG. 3. Thus, the feeding air stream 23 can flow in through the first opening and out through the second opening. The second opening is fluidically connected or connectable to the feeding path 20. to The feeding path 20 is formed by or comprises here preferably a channel 28 within the piercing member 7 and/or insert 17 for guiding the air with entrained inhalation formulation. The channel 28 is preferably at least essentially straight and/or opens to the mixing zone 22 in the present embodiment.

The channel 28 may taper towards its outlet end. However, the channel 28 may also have essentially a constant inner diameter or cross sectional area or taper in the opposite direction.

The channel 28 is preferably cylindrical or circular in cross section. However, the channel 28 may also be oval. The same applies for the outlet tube 18 and/or mouthpiece 8.

In the present embodiment, the bypass path 21 leads through or is formed by at least one or two preferably tangential or radial bypass channels 29, preferably formed by the insert 17, connected to the mixing zone 22 and/or a preferably common mixing chamber or outlet channel 30. Here, the outlet channel 30 has a larger diameter than channel 28. However, other constructional solutions are possible.

Preferably, the outlets of the feeding path 20 (channel 28) and of the bypass path 21 (bypass channels 29) are located as close as possible.

In the present embodiment, the bypass path 21 opens radially and/or tangentially with its outlet(s) into the preferably centrally arranged feeding path 20, channel 28, outlet channel 30 and/or mixing zone 22. However, other constructional solutions are possible.

The inhaler 1 comprises preferably an impaction element 31 for impaction and/or deflection of the air stream 9 with entrained inhalation formulation. In particular, the feeding air stream 23 with entrained inhalation formulation can impact onto the impaction element 31 and/or is deflected by the impaction element 31.

In particular, the impaction element 31 is located centrally in alignment of the feeding path 20 or channel 28 or 30 and/or covers the feeding path 20/channel 28 radially or transversally to the main or outlet direction. Thus, at least the feeding air stream 23 is deflected and/or has to surround the impaction element 31.

In the present embodiment, the impaction element 31 comprises an impaction surface 32 inclined to the main or outlet direction of the feeding path 20, channel 28 and/or mouthpiece 8. In particular, the impaction element 31 or its impaction surface 32 is at least essentially conical.

Preferably, the impaction element 31 is stationary. However, it is also possible that the impaction element 31 is moveable.

Preferably, the impaction element 31 is located within the mouthpiece 8, preferably within or adjacent to the insert 17 and/or the feeding path 20, mixing zone or chamber 22 and/or outlet channel 30. in the present embodiment the impaction element 31 is located at the end or downstream the feeding path 20. The impaction element 31 is preferably attached to a tube or wall 33, preferably of the feeding path 20 or insert 17 or mixing chamber 22 or outlet channel 30, in particular by means of ribs (not shown) or the like.

Figure 3:
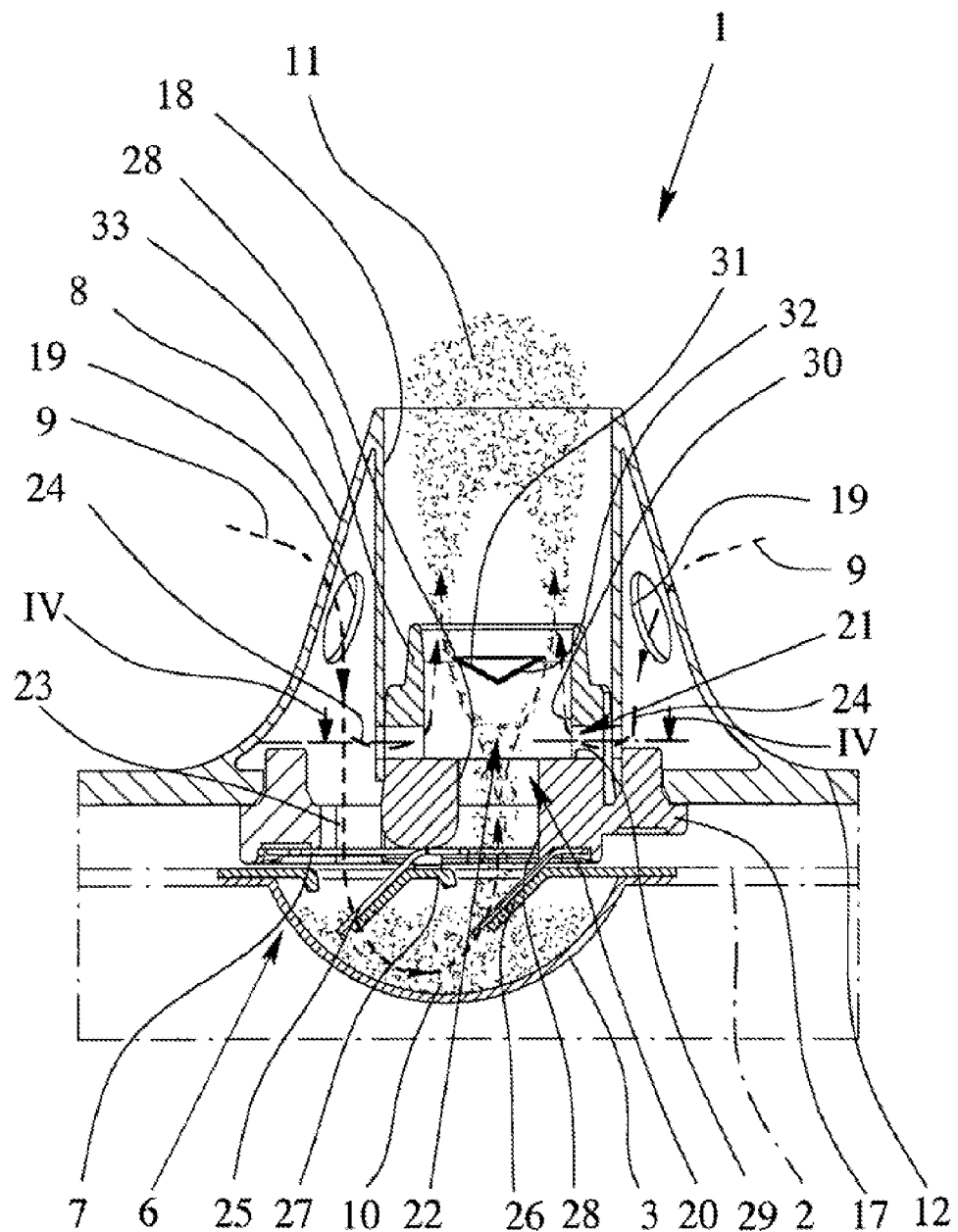

It has to be noted that FIG. 3 shows only very schematically, in particular not in scale, a potential construction. Other constructional solutions are possible as well.

Figure 4:
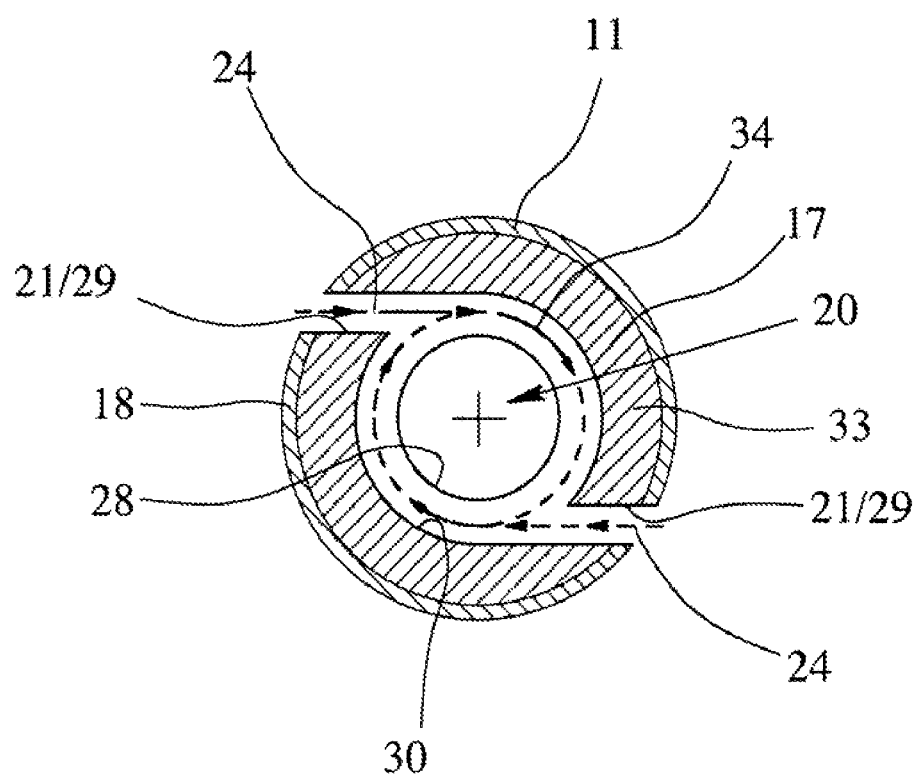

Preferably, the inhaler 1 comprises a (first) mixing means for generating a swirl or cyclone 34, in particular in the mouthpiece 8, feeding path 20, bypass path 21, outlet channel 30 and/or mixing zone 22 as schematically shown in the horizontal sectional view of the inhaler 1 in the area of the mouthpiece 8 according to FIG. 4.

Preferably, the mixing means is formed by or comprises the at least one or two bypass channels 29 feeding tangentially and/or transversely bypass air into the feeding air stream 23 or the mouthpiece 8, most preferably into the outlet channel 30, the mixing zone 22 and/or the feeding path 20. However, other constructional solutions are possible.

The mixing means allows or ensures better mixing of the feeding air with the inhalation formulation and/or of the bypass air with the feeding air. This supports better deagglomeration of the inhalation formulation. In particular, the swirl or cyclone 34 generated by the mixing means supports deagglomeration of in particular larger particles of the inhalation formulation.

Most preferably, the mixing means forms or defines the mixing zone 22.

In the present embodiment, the impaction element 31 and the mixing means are preferably combined. Then, any intermediate wall between channel 28 and channel 30, i.e. between the feeding path 20 and the bypass path 21, may be omitted. Alternatively or additionally, the impaction element 31 is preferably located downstream the mixing means and/or the mixing zone 22.

However, it is also possible to provide only one of the impaction element 31 and mixing means.

Figure 5:
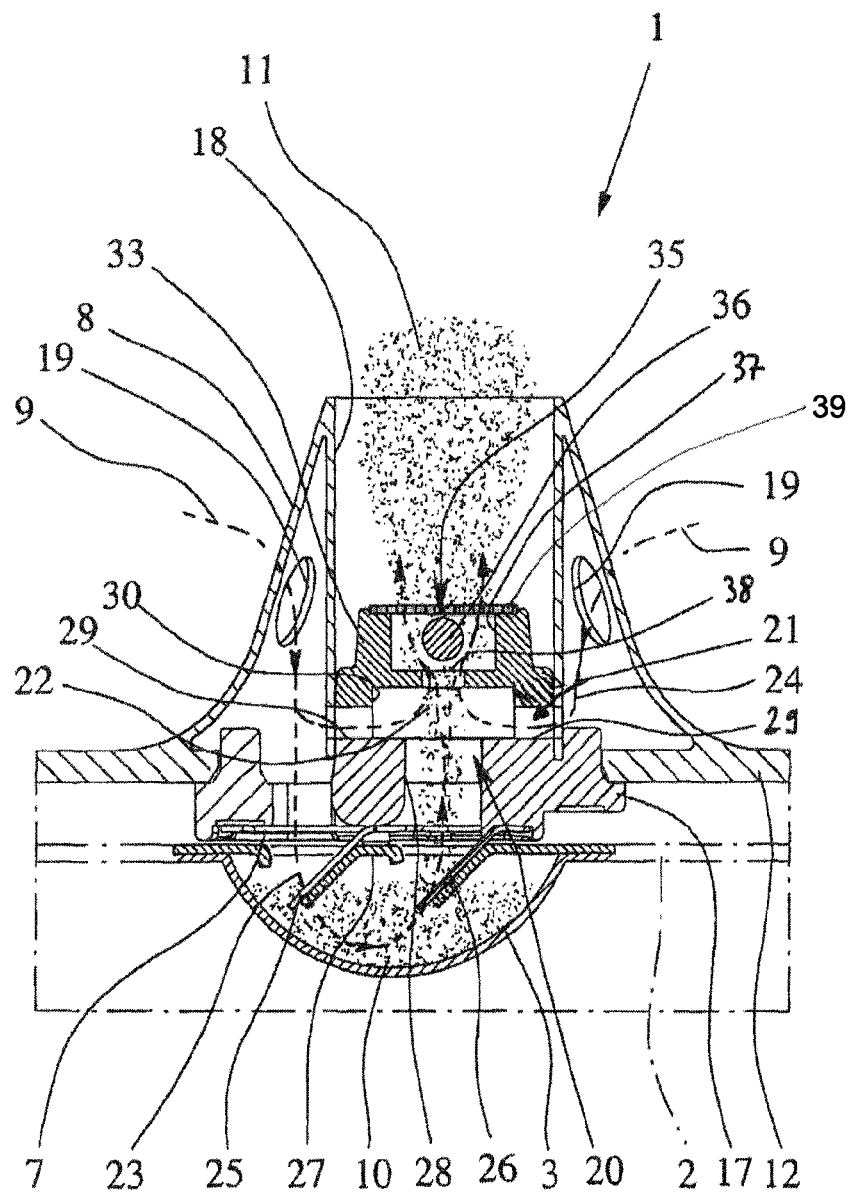

FIG. 5 shows in a schematically sectional view similar to FIG. 3 another preferred embodiment of the inhaler 1 according to the present invention. The following description focuses on relevant differences so that the previous descriptions, advantages, aspects and/or features preferably apply in addition or in a similar manner.

Alternatively or additionally to the impaction element 31, the inhaler 1 comprises an oscillating and/or vibrating device 35 which is also preferably used in combination with the mixing means, but could also be used separately.

The oscillating and/or vibrating device 35 is located or realized separately from the reservoir formed by the blister strip 2. It supports de-agglomeration of the inhalation formulation and/or generates vibrations, in particular vibrates the blister strip 2, the blister pocket 3, the feeding path 20, the piercing member 7 and/or any other element or component of the inhaler 1. Due to the vibrations, better or quicker loosening and/or de-agglomeration of the inhalation formulation can be achieved.

The oscillating and/or vibrating device 35 preferably comprises an oscillating element 36, which is preferably moveable by the air stream 9. In particular, the element 36 is set in vibration or oscillation by means of the feeding air stream 23 and/or bypass air stream 24.

The element 36 is preferably essentially ball-like, in particular a ball. However, it can have any other suitable form, for example a longitudinal, egg-like or any similar form. In particular, it is possible to tune the oscillating/vibration frequency by variation or adaptation of the mass, density and/or form of element 36.

Preferably, the element 36 is located in an oscillation chamber 37, preferably fanned by or in the feeding 20, mixing zone 22, channel 30 or insert 17 or any other suitable component of the inhaler 1. The air stream 9, 23 and/or 24 can be supplied via a supply opening or channel 38 to the chamber 37. In particular, the supply channel 38 is connected to or formed by the feeding path 20 or channel 30 or insert 17 or any other suitable component of the inhaler 1.

The supply channel 38 opens preferably to the oscillation chamber 37 with a cross section that is preferably smaller than a cross section of the chamber 37 and element 36. The oscillation chamber 37 is preferably blocked by a cover or blocking means 39, e.g. a grid, rib or the like, so that the element 36 cannot escape from the chamber 37. However, other arrangements and/or fluidic connections are also possible.

The element 36 can preferably freely move in chamber 37 and/or is moved back and forth by the air stream 9, 23, 24 flowing through the chamber 31 and, in particular set in oscillation, namely preferably along the main flow direction. Most preferably, the geometrical dimensions are similar or correspond to the respective measures given in EP 0 147 755 A2 which is herewith introduced for additional disclosure and as reference.

The oscillation of the element 36 is preferably caused by the so-called Bernoulli effect. When oscillating, preferably the element 36 periodically or repeatedly hits the opening of the supply channel 38 and/or the blocking means 39. Thus, different effects may result which support de-agglomeration and dispensing of the inhalation formulation.

One effect is that the oscillation of element 36 causes turbulences or eddies or the like in the chamber 37 which may enhance mixing and/or de-agglomeration.

Another effect of the element 36 is that it forms a hindrance or obstacle that has to be surrounded by the air stream 9 with the entrained inhalation formulation. The element 36 may form a deflector and/or impactor. In particular, larger particles of the inhalation formulation may impact onto the element 36 or may be deflected. by the element 36 so that de-agglomeration is enhanced.

A further effect is that the oscillating element 36 generates a vibration such that the inhaler 1, the mouthpiece 8, the outlet tube 18, the feeding path 20, the piercing member 7, the blister pocket 3 and/or at least part of one of these or other components vibrate. This enhances loosening and dc-agglomeration of the inhalation formulation. In particular, the blister pocket 3, e.g. its lid 27 and/or its base, can be set in vibration.

According to an additional effect, the oscillating and/or vibrating device 35 or its oscillating element 36 may generate air pressure variations or waves or oscillations resulting in better loosening or de-agglomeration of the inhalation formulation in particular, in the opened blister pocket 3.

The above effects can be achieved or realized independently from each other and/or in any combinations thereof or altogether.

The oscillating and/or vibrating device 35 is preferably located within the mouthpiece 8, outlet tube 18, insert 17, feeding path 20, mixing zone 22, outlet channel 30 or downstream thereof.

The oscillating and/or vibrating device 35 or element 36 preferably oscillates or vibrates with a vibration frequency of about 20 Hz to 500(1 Hz, preferably 50 Hz to 500 Hz.

Most preferably, the mixing means and the oscillating/vibrating device 35 are combined. This results in very effective de-agglomeration and, in is particular, in a generation of an aerosol cloud 11 with at least essentially only fine particles of the inhalation formulation.

Preferably, the oscillating and/or vibrating device 35 is located downstream of the mixing means. However, any other arrangement is also possible.

Figure 6:
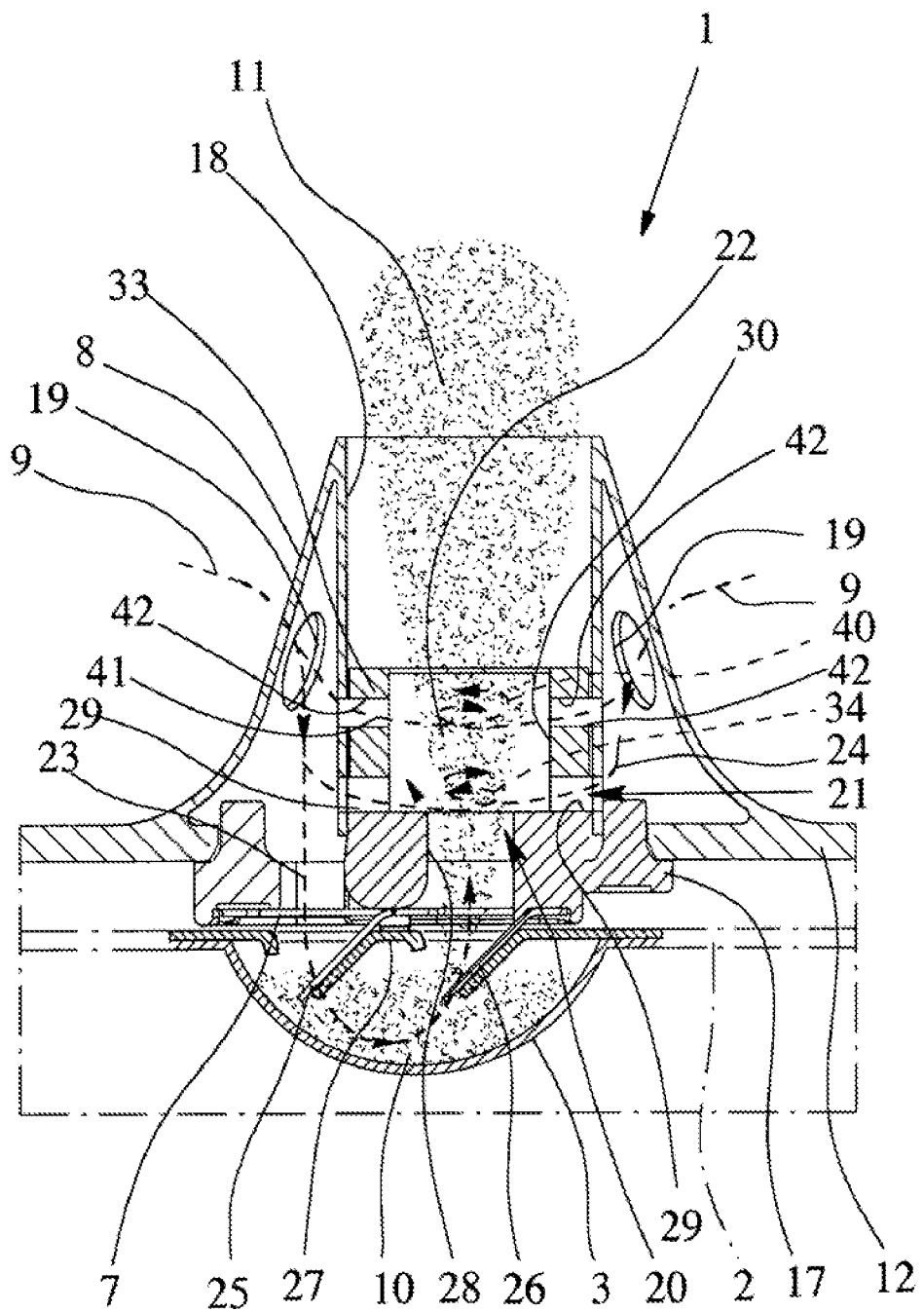

FIG. 6 shows a further preformed embodiment of the inhaler 1 according to the present invention in a schematic sectional view similar to FIGS. 3 and 5. The following description focuses also only on main differences between this embodiment and the previous embodiments. The previous descriptions, advantages, aspects and/or features preferably apply in addition or in a similar manner.

The inhaler 1 comprises a second mixing means for generating a second swirl or cyclone 40 as schematically shown in FIG. 6. Preferably, the second mixing means is constructed in a similar manner as the first mixing means.

The second mixing means mixes in particular a second bypass air stream 41 with the feeding air stream 23 and/or generates the second cyclone 40 in the feeding path 20, insert 17, channel 30 and/or mixing zone or chamber 22 where the feeding air stream 23 and second bypass air stream 41 are or have been mixed.

In the present embodiment, the second mixing means comprises preferably at least one or two second bypass channels 42 feeding tangentially and/or transversally bypass air into the feeding path 20 or mixing chamber or the feeding air stream 23 already mixed with the first bypass air stream 24, in particularly downstream of the first mixing means/bypass channels 29.

Preferably, the second bypass channels 42 open to the feeding path 20, mixing chamber or outlet tube 18, in particular tangentially and/or transversally to the main flow or dispensing direction of the feeding path 20 or mouthpiece 8 or outlet tube 18.

The turbulences generated by the mixing means may result in lowering the mean velocity of the generated aerosol cloud 11. A lower mean velocity is usually preferred, and, thus, improved discharged characteristics can be achieved.

Preferably, the first mixing means generates the first cyclone 34 with a first direction of rotation and the second mixing means generates the second cyclone 40 with a second direction of rotation opposite the first one. This counter rotation results in optimized de-agglomeration of the inhalation formulation, in particular of larger particles of the inhalation formulation. This may be explained due to high shear forces and/or turbulences or the like.

The two mixing means or its generated cyclones 34, 40 are preferably located one after the other or one above the other, in particular axially spaced or axially one above the other with respect to the main feeding direction or dispensing direction or main extension of the feeding path 20 or outlet tube 18 or mouth piece 8. However, other arrangements are also possible.

It has to be noted that the two mixing means as described above are preferred. However, two mixing means are not necessarily required, but preferred in combination.

It has to be noted that FIGS. 3, 5 and 6 are only schematic sections and show the bypass channels 29, 42 in the same plane although the channels 29, 42 are preferably transversally offset relation to each other to generate the cyclones 34, 40 with the desired direction of rotation.

Individual features and aspects of the described embodiments and alternatives may be combined as desired.

Preferably, the terms "blister strip" and "blister pockets" have to be understood in a very broad sense to cover also other kinds of storage means with receptacles or even bulk storages for the formulation.

| List of reference numbers | |
|---|---|
| 1 | inhaler |
| 2 | blister strip |
| 3 | blister pocket |
| 4 | reservoir |
| 5 | conveyor |
| 5a | onward movement |
| 6 | opening and/or removal position |
| 7 | piercing member |
| 8 | mouthpiece |
| 9 | air stream |
| 10 | powder |
| 11 | aerosol cloud |
| 12 | actuator |
| 12a | housing |
| 13 | receiving apparatus |
| 14 | conveying wheel |
| 15 | mouthpiece cover |
| 16 | cover axis |
| 17 | insert |
| 18 | outlet tube |
| 19 | air opening |
| 20 | feeding path |
| 21 | bypass path |
| 22 | mixing zone |
| 23 | feeding air stream |
| 24 | bypass air steam |
| 25 | first piercing element |
| 26 | second piercing element |
| 27 | lid |
| 28 | channel |
| 29 | bypass channel |
| 30 | outlet channel |
| 31 | impaction element |
| 32 | impaction surface |
| 33 | wall |
| 34 | first cyclone |

-continued

| List of reference numbers | |
|---|---|
| 35 | oscillating/vibrating device |
| 36 | oscillating element |
| 37 | oscillation chamber |
| 38 | supply channel |
| 39 | blocking means |
| 40 | second cyclone |
| 41 | second bypass air stream |
| 42 | second bypass channel |

The invention claimed is:

1. An inhaler (1) for delivery of an inhalation formulation from a blister strip (2) with a plurality of blister pockets (3) containing the inhalation formulation in doses, wherein the inhaler (1) comprises:

a conveyor (5) for stepwise onward movement of the blister strip (2), and/or a piercing member (7) to puncture a lid (27) of an aligned blister pocket (3), the inhaler (1) being designed such that an air stream (9) of ambient air can be sucked or delivered by breathing during inhalation in order to discharge the respective dose from an opened blister pocket (3) and to deliver the respective dose with the ambient air as an aerosol cloud (11) via a mouthpiece (8), and the inhaler (1) comprises an oscillating and/or vibrating device (35) separate from the blister strip (2) for supporting de-agglomeration of the inhalation formulation and/or for vibrating at least part of the blister strip (2) and/or a piercing member (7) or any other component of the inhaler (1), wherein the oscillating and/or vibrating device (35) is located within the mouthpiece (8), within a feeding path (20) or downstream thereof, the oscillating and/or vibrating device (35) comprises an oscillating element (36), or is formed by the oscillating element (36), and the oscillating element (36) is located within a main flow of the feeding path and oscillates by moving back and forth along a longitudinal axis of the mouthpiece in the main flow direction of the feeding path (20) or mouthpiece (8).

2. The inhaler according to claim 1, wherein a first mixing means is located upstream the oscillating and/or vibrating device (29).

3. The inhaler according to claim 1, wherein the oscillating and/or vibrating device (35) is operated by the air stream (9).

4. The inhaler according to claim 1, wherein the oscillating element (36) forms an impactor or deflector for the air stream (9) and/or entrained inhalation formulation.

5. The inhaler according to claim 1, wherein the oscillating element (36) is moveable freely in a chamber (37) connected to the feeding path (20) or formed by the feeding path (20).

6. The inhaler according to claim 1, wherein the oscillating and/or vibrating device (35) uses the Bernoulli effect.

7. The inhaler according to claim 1, wherein the inhaler (1) is designed such that the oscillating and/or vibrating device (35) or its oscillating element (36) oscillates or vibrates with a frequency of 20 Hz to 5000 Hz.

8. The inhaler according to claim 1, wherein the oscillating and/or vibrating device (35) is located downstream of the mixing of a feeding air stream (23) with a bypass air stream (24).

9. The inhaler according to claim 1, wherein the inhaler (1) comprises a molded and/or unitary insert (17) holding or forming the piercing member (7), wherein the insert (17) contains, comprises or forms the oscillating and/or vibrating device (35) and/or a first and/or a second mixing means.

10. The inhaler according to claim 1, wherein the oscillating element (36) is a ball.

11. The inhaler according to claim 1, wherein the oscillating element oscillates by moving back and forth along a center longitudinal axis of the mouthpiece.

* * * * *